(12) United States Patent
Pohl et al.

(10) Patent No.: US 10,495,614 B2
(45) Date of Patent: Dec. 3, 2019

(54) VIAL CAP AND METHOD FOR REMOVING MATRIX COMPONENTS FROM A LIQUID SAMPLE

(71) Applicant: DIONEX CORPORATION, Sunnyvale (CA)

(72) Inventors: Christopher A. Pohl, Union City, CA (US); Rosanne W. Slingsby, Pleasanton, CA (US)

(73) Assignee: Dionex Corporation, Sunnyvale, CA (US)

( * ) Notice: Subject to any disclaimer, the term of this patent is extended or adjusted under 35 U.S.C. 154(b) by 491 days.

(21) Appl. No.: 14/586,339

(22) Filed: Dec. 30, 2014

(65) Prior Publication Data

US 2016/0187306 A1 Jun. 30, 2016

(51) Int. Cl.
| | |
|---|---|
| *G01N 30/60* | (2006.01) |
| *G01N 30/96* | (2006.01) |
| *G01N 30/14* | (2006.01) |
| *B01L 3/00* | (2006.01) |
| *G01N 30/24* | (2006.01) |
| *G01N 30/00* | (2006.01) |

(52) U.S. Cl.
CPC ......... *G01N 30/6004* (2013.01); *G01N 30/14* (2013.01); *G01N 30/6065* (2013.01); *G01N 30/96* (2013.01); *B01L 3/502* (2013.01); *G01N 30/24* (2013.01); *G01N 2030/009* (2013.01); *G01N 2030/143* (2013.01)

(58) Field of Classification Search
CPC .............. B01L 3/502; G01N 2030/009; G01N 2030/143; G01N 30/14; G01N 30/24; G01N 30/6004; G01N 30/6065; G01N 30/96

See application file for complete search history.

(56) References Cited

U.S. PATENT DOCUMENTS

| | | | |
|---|---|---|---|
| 4,263,407 | A | 4/1981 | Reed, Jr. |
| 4,644,807 | A | 2/1987 | Mar |
| 5,324,752 | A | 6/1994 | Barretto et al. |
| 7,303,671 | B2 | 12/2007 | Srinivasan et al. |
| 2002/0198271 | A1 | 12/2002 | Thunhorst et al. |

(Continued)

FOREIGN PATENT DOCUMENTS

| | | |
|---|---|---|
| CN | 1313790 A | 9/2001 |
| EP | 0385587 B1 | 12/1993 |

(Continued)

OTHER PUBLICATIONS

Dionex AS-DV Autosampler Operator's Manual, Document No. 065259, Rev. 04, Dec. 2011, 130 pages.

(Continued)

*Primary Examiner* — Samuel P Siefke
(74) *Attorney, Agent, or Firm* — Timothy J. Ohara; David A. Schell

(57) ABSTRACT

A vial cap for removing a matrix component from a liquid sample is described. The vial cap includes a cap body, an inlet portion, and an outlet portion. The cap body is configured to have a slidable gas and liquid seal with a side wall of a sample vial. The inlet portion includes a counterbore section that holds a filter plug. The filter plug includes a polyethylene resin and a material selected from the group consisting of an ion exchange material and a reversed-phase material. The vial cap is adapted for solid phase extraction for use in an autosampler with a plurality of sample vials.

6 Claims, 3 Drawing Sheets

(56) References Cited

U.S. PATENT DOCUMENTS

| | | |
|---|---|---|
| 2003/0062311 A1 | 4/2003 | Yao et al. |
| 2005/0023212 A1 | 2/2005 | Inoue et al. |
| 2010/0224012 A1 | 9/2010 | Modic et al. |
| 2011/0259818 A1 | 10/2011 | Tamada et al. |

FOREIGN PATENT DOCUMENTS

| | | |
|---|---|---|
| EP | 0659482 A1 | 6/1995 |
| JP | 10300652 A | 11/1998 |
| JP | 3015870 B2 | 3/2000 |
| JP | 2009062512 A | 3/2009 |
| WO | 2004007081 A1 | 1/2004 |
| WO | 2010120977 A1 | 10/2010 |
| WO | WO2013151654 A1 | 10/2013 |

OTHER PUBLICATIONS

Dionex Product Manual ASRS(R) 300 CSRS(R) 300, Document No. 031956, Rev. 05, Aug. 2007, 51 pages.
Dionex Product Manual for IonPac(R) AG11 IonPac(R) AS11, Doc No. 034791, Rev. 12, Apr. 7, 2009, 46 pages.
Dionex Product Manual for IonPac(R) CG12A IonPac(R) CS12A, Doc No. 031132, Rev. 09, May 2010, 78 pages.

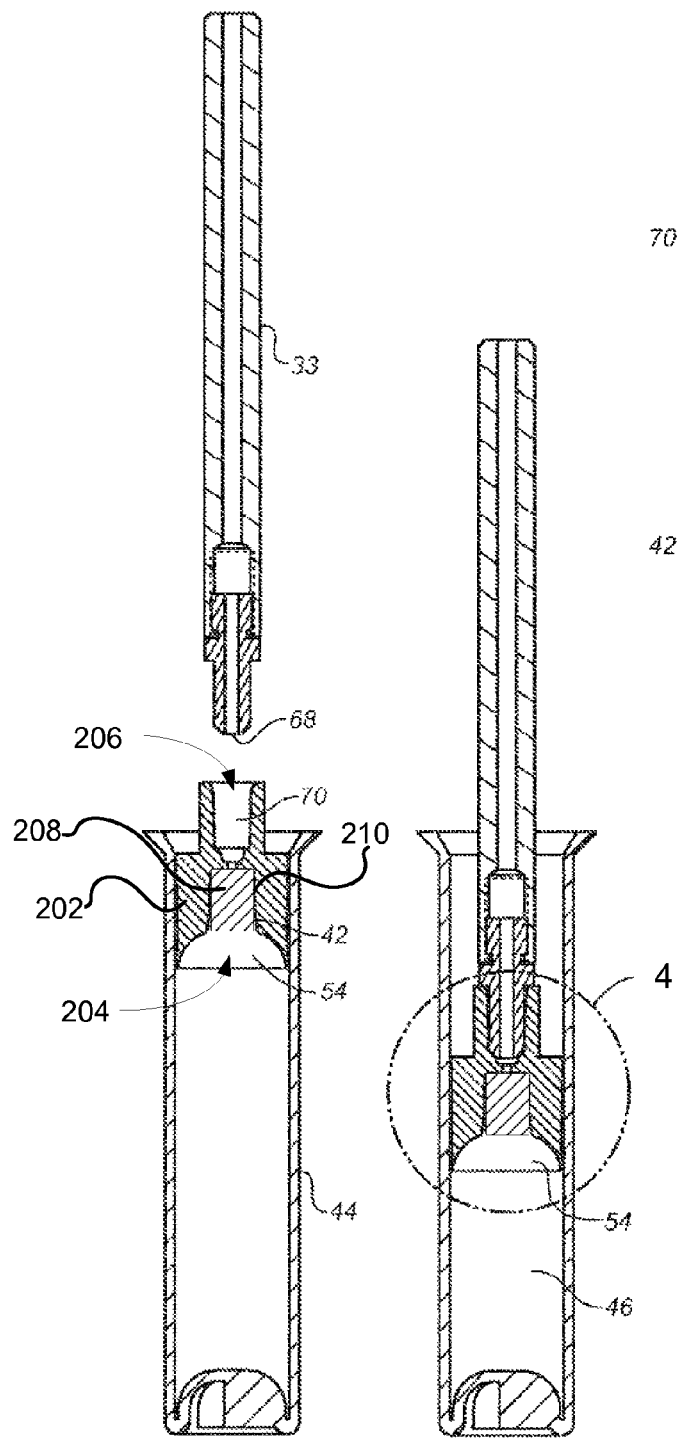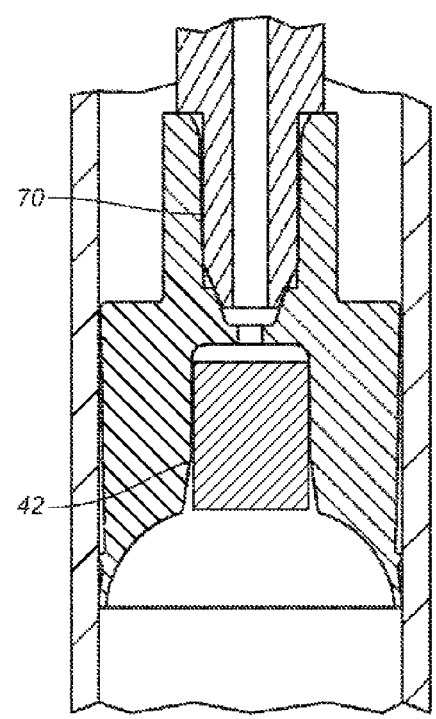
FIG. 2   FIG. 3   FIG. 4

VIAL CAP AND METHOD FOR REMOVING MATRIX COMPONENTS FROM A LIQUID SAMPLE

BACKGROUND

Chromatography is a widely used analytical technique for the chemical analysis and separation of molecules. Chromatography involves the separation of one or more analyte species from other matrix component present in a sample. A stationary phase of a chromatography column is typically selected so that there is an interaction with the analyte. Such interactions can be ionic, hydrophilic, hydrophobic, or combinations thereof. For example, the stationary phase can be derivatized with ionic moieties that ideally will bind to ionic analytes and matrix components with varying levels of affinity. A mobile phase is percolated through the stationary phase and competes with the analyte and matrix components for binding to the ionic moieties. The mobile phase is a term used to describe a liquid solvent or buffer solution that is pumped into a chromatography column inlet. During this competition, the analyte and matrix components will elute off of the stationary phase as a function of time and then be subsequently detected at a detector. Examples of some typical detectors are a conductivity detector, a UV-VIS spectrophotometer, and a mass spectrometer. Over the years, chromatography has developed into a powerful analytical tool that is useful for creating a healthier, cleaner, and safer environment where complex sample mixtures can be separated and analyzed for various industries such as water quality, environmental monitoring, food analysis, pharmaceutical, and biotechnology.

Under certain circumstances, a sample can have a relatively high concentration of a matrix component compared to the analyte concentration. This can cause an interference and prevent an accurate analysis of the analyte within the sample. In one instance, an excessively high matrix concentration can saturate the conductivity detector skewing the baseline response of the analyte peak of a chromatogram. In another instance, a matrix component can generate a chromatographic peak that overlaps with the analyte peak, and thus, interfere with the analysis. An example of matrix component can be an ion such as chloride in the trace analysis of perchlorate. As such, the liquid sample will typically be pre-treated to remove or reduce a high concentration of a matrix component like chloride. Another example of a matrix component can be a hydrophobic species such as sodium lauryl sulfate in the analysis of anions such as chloride and sulfate.

Solid phase extraction is a type of sample pre-treatment that can be used to remove matrix component from a sample. Some solid phase extraction devices require a significant amount of pressure to pass a liquid sample through the solid phase extraction device, which is not well-suited to automated sample pre-treatment with auto-samplers. Other solid phase extraction devices that do not require a significant amount of pressure cannot bind a significant amount of matrix component because of low capacity. A relatively low dead volume is useful where there is a limited volume of a sample to pre-treat. Thus, Applicant believes that there is a need for solid phase extraction materials that have a high capacity per unit volume sufficient to pre-treat a single sample, require a relatively low pressure (i.e., less than 100 PSI), and have a compact size so that it can be adapted to existing auto-sampling instruments. Applicant also believes that the extraction material should be low cost so that it is single use and disposable circumventing the need to clean the extraction material after the extraction.

SUMMARY

A vial cap for removing a matrix component from a liquid sample and transferring the liquid sample in a sample vial to an injection valve at the same time is described. The vial cap includes a cap body, an inlet portion, and an outlet portion. The cap body includes a liquid sample passageway, and an outer periphery configured to have a slidable gas and liquid seal with a side wall of a sample vial. The sample vial includes a side wall, a bottom wall, and an inlet opening. The inlet portion is configured to receive a pressurized liquid sample from the sample vial where the liquid sample flows into the liquid sample passageway. The inlet portion includes a counterbore section. The counterbore section can hold a filter plug. The filter plug includes a polyethylene resin and a material selected from the group consisting of an ion exchange material and a reversed-phase material. In another embodiment, the material may be a combination of an ion exchange material and a reversed-phase material. The outlet portion can be configured to output the liquid sample from the liquid sample passageway that has passed through the filter plug. The outlet portion includes a plunger section configured to receive a downward force into a sample vial to pressurize the liquid sample within the sample vial. The matrix component is selected from the group consisting of an ionic species, a hydrophobic species, and a combination thereof.

In regards to the vial cap described above, the reversed-phase material is configured to bind an ion pairing agent. The reversed-phase material is also configured to bind the matrix component where the matrix component is hydrophobic.

In regards to the vial cap described above, the polyethylene resin can include a high density polyethylene and the ion exchange material can include a crosslinked styrene sulfonate. Alternatively, the polyethylene resin can include a high density polyethylene and the ion exchange material can include a crosslinked copolymer of a vinylbenzylchloride and a divinylbenzene where the crosslinked copolymer is quaternized with a trimethylamine. In another embodiment, the polyethylene resin can include a high density polyethylene and the ion exchange material can include a crosslinked copolymer of a chloromethylated styrene quaternized with a tertiary amine and a divinylbenzene.

In regards to the vial cap described above, the polyethylene resin can include a high density polyethylene and the reversed-phase material can include a divinylbenzene resin treated with an ion pairing agent selected from the group consisting of a hexane sulfonate, octane sulfonate, dodecane sulfonate, tetrapropylammonium, tetrabutylammonium, tetrapentylammonium, trifluoroacetate, heptafluorobutyrate, dodecylsulfate, and combinations thereof.

In regards to the vial cap described above, the polyethylene resin can include a high density polyethylene and the ion exchange material can include a crosslinked styrene sulfonate treated with an anion exchange latex.

In regards to the vial cap described above, the polyethylene resin can include a high density polyethylene and the ion exchange material can include a positively charged crosslinked polymer treated with a cation exchange latex. The positively charged crosslinked polymer is selected from the group consisting of a copolymer of a vinylbenzylchloride and a divinylbenzene where the crosslinked copolymer that is quaternized with a trimethylamine, and a crosslinked copolymer of a chloromethylated styrene quaternized with a tertiary amine and a divinylbenzene.

In regards to the vial cap described above, the plunger section is a socket configured to receive a plunger. The plunger is configured to apply a downward force to the vial cap and transfer the liquid sample through a hollow portion of the plunger.

A method of removing a matrix component from a liquid sample is described using one of the above described vial caps. The method includes adding the liquid sample to a sample vial. The vial cap is pushed through the inlet opening of the sample vial towards the bottom wall to pressurize the liquid sample within the sample vial. The liquid sample is displaced into the inlet portion, through the filter plug, and out of the outlet portion. At the same time of the displacing, a portion of the matrix component is removed from the liquid sample with the filter plug.

In regards to the above method, the pressure within the sample vial is less than 100 PSI.

In regards to the above method, it further includes disposing the vial cap along with the filter plug.

In regards to the above method, the liquid sample includes particles, and the method further includes the removing of a portion of the particles from the liquid sample with the filter plug.

In regards to the above method, the removed portion of the matrix component is greater than 50% of the matrix component present in the liquid sample before the liquid sample displacing.

In regards to the above method, it further includes loading a sample loop on an injection valve with the displaced liquid sample. The liquid sample can then be injected in the sample loop to a chromatographic separation device. At least one analyte is separated from the matrix components in the liquid sample on the chromatographic separation device. An analyte separated from the matrix components is detected at a detector.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 2 illustrates a cross-sectional view of a sample delivery needle, a vial cap, and a sample vial where the vial cap and the sample delivery needle are in an unengaged state.

FIG. 3 illustrates a cross-sectional view of the sample delivery needle engaged with the vial cap where the sample delivery needle is partially deployed to dispense fluid out of the sample vial.

FIG. 4 shows an expanded cross-sectional view of the sample delivery needle engaged with the vial cap that illustrates a position of a filter plug that removes matrix components. The expanded cross-sectional view of FIG. 4 approximately corresponds to circle 4 of FIG. 3.

DETAILED DESCRIPTION OF EMBODIMENTS

Figure 1:
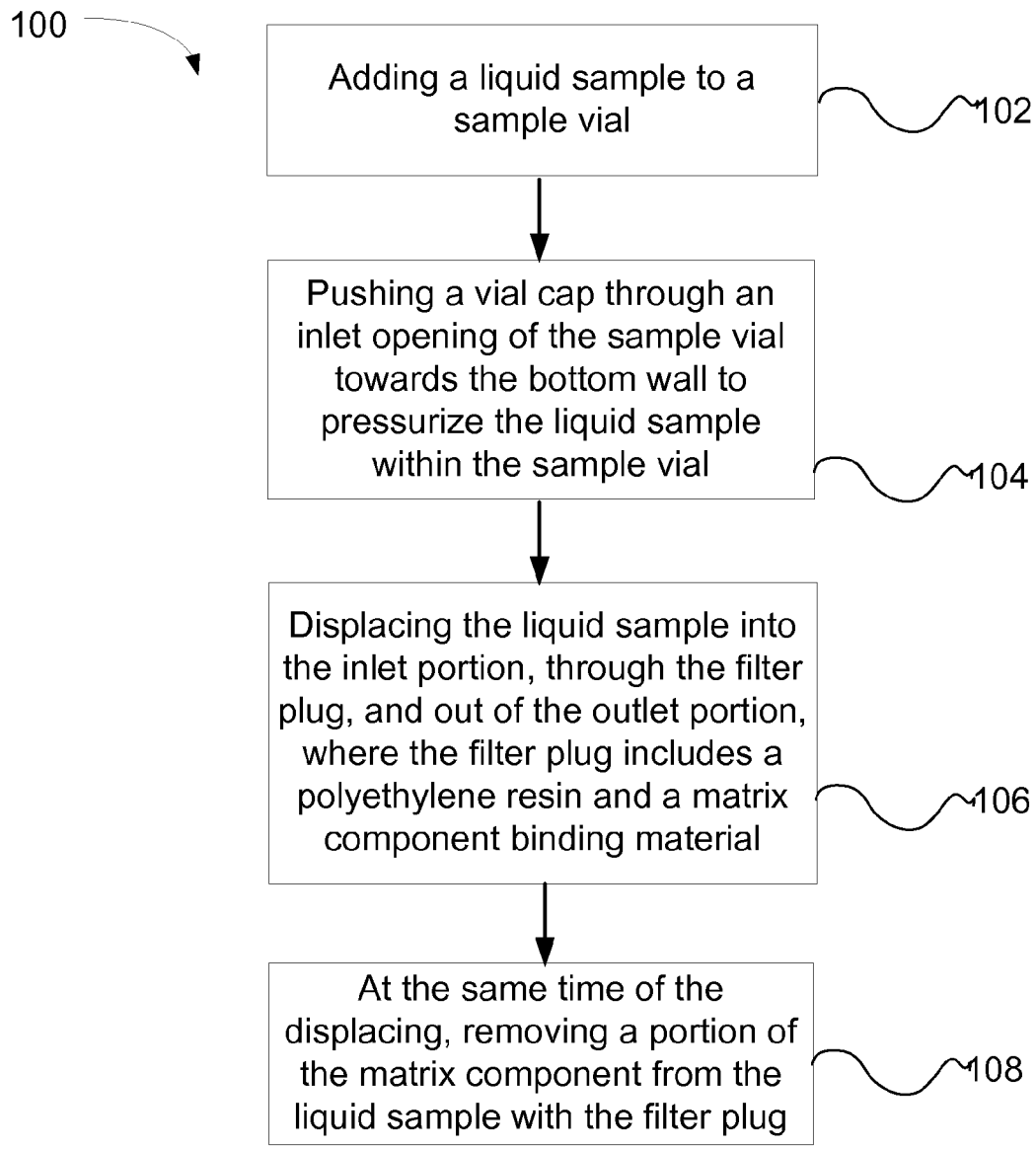
FIG. 1 is a flow chart illustrating a method of removing a matrix component from a liquid sample using a vial cap containing a filter plug.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

A filter plug can be a porous material used to filter a liquid sample. In an embodiment, matrix components can be retained by the filter plug so that the filtered liquid sample (i.e., filtrate) has a substantial portion of the matrix components removed. In an embodiment, a substantial portion or substantially all may represent greater than 50%. In addition to removing matrix components, the filter plug can also remove particles from the liquid sample at the same time. The filter plug can include a polyethylene resin and a material such as an ion exchange material, a reversed-phase material, or a combination thereof. The ion exchange material may be an anion exchange material or a cation exchange material. The ion exchange material is configured to bind anions or cations from the liquid sample. The reversed-phase material is configured to bind hydrophobic material from the liquid sample.

In an embodiment, polyethylene resin can be in the form of particles, which are fused together at elevated temperatures to bind ion exchange particles or reversed-phase particles. The polyethylene resin may be a high density polyethylene (HDPE). The density of HDPE can range from 0.93 to 0.97 g/cm$^3$. Although the density of HDPE is only marginally higher than that of low density polyethylene (LDPE), HDPE has little branching, giving it stronger intermolecular forces and tensile strength than LDPE. In an alternative embodiment to HDPE resin, other materials that may be suitable for use in the filter plugs described herein include polypropylene resin, polytetrafluoroethylene (PTFE), polyvinylidene fluoride (PVDF), ethyl vinylacetate (EVA), polycarbonate and polycarbonate alloys, nylon 6, thermoplastic polyurethane (TPU), and polyether sulfone (PES).

The ion exchange resin may be one of the following types such as a strong cation exchange, weak cation exchange, strong anion exchange, and weak anion exchange. In an embodiment of a cation exchange resin, the resin may be in a salt form of a cation exchange resin such as, for example, a sodium form.

The ion exchange resin includes a substrate that is insoluble in water and typically in the form of approximately spherical beads. In an embodiment, the beads may have a diameter ranging from about 2 microns to about 100 microns, preferably ranging from about 2 microns to about 50 microns, and more preferably ranging from about 10 microns to about 35 microns. The ion exchange resin may have a pore size ranging from about 10 angstroms to about 2000 angstroms.

In an embodiment, the ion exchange material may include a crosslinked styrene sulfonate particle. As an example, the particle size can be about 35 microns in diameter and be in the sodium form. The sulfonate groups on the particles act as the cation exchange groups.

In regards to anion exchange material, a crosslinked copolymer of a vinylbenzylchloride and a divinylbenzene can be used where the crosslinked copolymer is quaternized with a tertiary amine. Alternatively, the anion exchange material can be prepared via chloromethylation of a crosslinked copolymer of styrene and divinylbenzene where the crosslinked copolymer is quaternized with a tertiary amine. Examples of tertiary amines are trimethylamine and dimethylethanolamine. As an example, the particle size can be about 35 microns in diameter and be in the chloride form.

In an embodiment, the reversed-phase material may be a copolymer of styrene and divinyl benzene. More broadly, the reversed-phase polymer can be synthesized from a wide variety of polyunsaturated monomers including divinylbenzene, trivinylbenzene and the like, and the preferred monoethylenically unsaturated monomers including styrene, the o, m, and p-methyl styrenes, and o, m, and p-ethyl styrenes, ethylvinylbenzene, vinylnaphthalene and vinyltoluene. Suitable reversed-phase polymers can also be derived from aliphatic polyunsaturated monomers such as diacrylates and dimethacrylates, including ethylene glycol diacrylate, ethylene glycol dimethacrylate, trimethylolpropane trimethacrylate, neopentyl glycol dimethacrylate, divinylketone, divinyl sulfide, allyl acrylate, diallyl maleate, diallyl fumarate, and the like. Such reversed-phase polymers can also be synthesized as copolymers with monoethylenically unsaturated aliphatic monomers include esters of acrylic acid, such as methyl, ethyl and propyl acrylate, and the corresponding esters of methacrylic acid, wherein the ester group contains 1-10 carbon atoms. The preferred reversed phase polymers are based on macroreticular copolymers of styrene and divinylbenzene (about 99-2 wt. % styrene, balance divinylbenzene). The foregoing ranges are on the basis of 100% active monomers. When commercial grades of divinylbenzene are used, about 20-50% of the divinylbenzene is ethylvinylbenzene and it is conventional to include the ethylvinylbenzene with the styrene or other monovinyl monomer when specifying the proportion of styrene or other monovinyl monomer. The reversed-phase material may also be based on surface chemical modification of inorganic materials such as silica, alumina, zirconia and the like such that the surface of the inorganic material is hydrophobic. Examples of such reversed phase materials based on inorganic substrates include porous silica particles which have been surface modified with any of a wide variety of commercially available alkylsilanes such as octadecylsilanes, dodecylsilanes, octylsilanes, butylsilanes or methylsilanes.

In another embodiment, the reversed-phase material may include a divinylbenzene resin treated with an ion pairing agent. Exemplary ion pairing may include hexane sulfonate, octane sulfonate, dodecane sulfonate, tetrapropylammonium, tetrabutylammonium, tetrapentylammonium, trifluoroacetate, or heptafluorobutyrate, dodecylsulfate. Other exemplary ion pairing agent may include alkyl sulfates where the alkane is between five and 18 carbons in length, alkyl sulfonates where the alkane is between five and 18 carbons in length, linear alkylbenzene sulfonates where the alkane substituent is between five and 18 carbons in length, branched alkylbenzene sulfonates where the alkane substituent is between five and 18 carbons in length, perfluorocarboxylic acids where the carbon backbone is between 1 and 12 carbons in length, symmetrical quaternary compounds where each of the four alkanes attached to the quaternary nitrogen is between five and 18 carbons in length, unsymmetrical quaternary compounds where three of the alkyl groups attached to the quaternary nitrogen are methyl substituents while the fourth alkyl group attached to the quaternary nitrogen is between five and 18 carbons in length, unsymmetrical quaternary compounds where two of the groups attached to the quaternary nitrogen are methyl substituents, a benzyl group is attached to the quaternary nitrogen and the fourth substituent group attached to the quaternary nitrogen is between five and 18 carbons in length, or unsymmetrical quaternary pyridinium compounds where the substituent group attached to the pyridinium nitrogen is between five and 18 carbons in length. It should be noted that the ion pairing agent can be in a salt form, an acid form, or a base form.

The ion pairing agent hexanesulfonic acid is an example that provides cation exchange functionality. Alternatively, the divinylbenzene resin can be treated with the ion pairing agent tetrabutylammonium hydroxide, which is an example that provides anion exchange functionality. The divinylbenzene resin can be a copolymer with materials such as divinylbenzene and polystyrene, and have a diameter of about 35 microns. The divinylbenzene resin is typically hydrophobic in nature. An ion pairing agent such as hexanesulfonic acid or tetrabutylammonium hydroxide can be paired to the hydrophobic surface of the divinylbenzene resin and create ion exchange sites. The filter plug can be made with polyethylene resin and divinylbenzene resin. Next, an ion pairing agent in a liquid solution can be filtered through the filter plug so that the ion pairing agent can attach to the divinylbenzene resin.

In another embodiment, the ion exchange material may include crosslinked styrene sulfonate particles treated with anion exchange latex. The anion exchange latex can include a quaternary amine group and have a diameter of about 360 angstroms. The filter plug can be made with polyethylene resin and crosslinked styrene sulfonate particle. Next, an anion exchange latex in a liquid solution can be filtered through the filter plug so that the latex can attach to the crosslinked styrene sulfonate particles. An example of anion exchange latex having quaternary amine groups can be found in U.S. Pat. No. 5,324,752, which is hereby incorporated by reference herein.

In another embodiment, the ion exchange material may include an anion exchange material such as a chloromethylated, crosslinked copolymer of styrene and divinylbenzene. The crosslinked copolymer is quaternized with a tertiary amine and subsequently treated with cation exchange latex. The cation exchange latex can include a sulfonated styrene group and have a diameter of about 200 nanometers. The filter plug can be made with polyethylene resin and an anion exchange material. Next, a cation exchange latex in a liquid solution can be filtered through the filter plug so that the latex can attach to the anion exchange particles. An example of cation exchange latex having sulfonated styrene groups can be found in U.S. Pat. No. 5,324,752, which is hereby incorporated by reference herein.

The matrix component binding material may be physically entrapped within a void volume in the fused polyethylene. Alternatively, the matrix component binding material can be bound to the polyethylene by a chemical bond or by an affinity to the polyethylene. In an embodiment, the polyethylene may be in the form of approximately spherical beads and fused together by heat. The matrix component binding material can be in the form of a resin substrate. As used herein, a resin or material can refer to a polymeric substrate and can be a plurality of particles.

The matrix component binding filter plugs can have a high capacity with a capacity per unit volume of greater than 0.05 milliequivalents per cubic centimeter (mEq/cc), and preferably ranging from about 0.14 mEq/cc to about 0.70 mEq/cc. The term milliequivalent refers to the equivalents of charged ions that can be bound to the matrix component binding filter plugs divided by a thousand.

In an embodiment, the matrix component binding filter plugs has a flow rate ranging from about 0.5 mL per minute to about 10 mL per minute, preferably from about 0.5 mL per minute to about 5 mL per minute, and more preferably from about 2 mL per minute to about 5 mL per minute at a pressure of 50 pounds per square inch or less where the matrix component binding filter plug is in the form of a cylinder with a diameter of about 5 millimeters and a length of about 10 millimeters.

The matrix component binding filter plugs can have a porosity ranging from about 50% to about 90%, where the porosity is based on the equation [(gram of water+gram of resin)/(gram of water+gram of resin+gram of organic phase)]×100%.

The matrix component binding filter plugs can also be characterized in terms of permeability. The matrix component binding filter plugs can have a range of approximately cylindrical sizes such as an outer diameter ranging from about 0.4 mm to about 20 mm, and a length ranging from about 6 mm to about 20 mm. The backpressure may be about 50 pounds per square inch and the flow rate through the matrix component binding filter plug may range from about 1 to about 5 mL/min. An equation for permeability can be calculated based on Equation 1.

$$\Delta p = u\eta L/B \qquad \text{(Eq. 1)}$$

The terms $\Delta p$ is a backpressure, u is a linear velocity of the sample flowing through the filter, $\eta$ is a viscosity of the liquid sample, L is a length of the filter, and B is a permeability of the matrix component binding filter plug. Based on Eq. 1 and the aforementioned parameters, the matrix component binding filter plugs can have a permeability ranging from about $1\times10^{-11}$ $m^2$ to about $1\times10^{-16}$ $m^2$.

Liquid samples can be filtered through the filter plugs described herein to remove matrix components from a sample in an automated format at low pressures and short cycle times. For convenience, the filter plugs can be relatively low cost, disposable, and have sufficient capacity to bind a substantial portion of matrix components for at least one sample aliquot. The following will describe a vial cap that is configured to hold the filter plug.

FIG. 2 illustrates a cross-sectional view of a plunger 33, a vial cap 54, and a sample vial 44 where vial cap 54 and plunger 33 are in an unengaged state. Plunger 33 is configured to bind to the vial cap 54. The vial cap 54 is configured to provide a seal at a side wall of the vial cap 54. Plunger 33 and the vial cap 54 together can be configured to have a piston cylinder mechanism with the sample vial 44 to dispense the liquid sample. A similar sample filtering apparatus is described U.S. Pat. No. 4,644,807 and US Pre-Grant Publication No. 20100224012, which are hereby incorporated by reference herein; however, the filter in this reference was used to remove particulates and/or reduce evaporation.

Referring to back to FIG. 2, vial cap 54 includes a cap body 202, an inlet portion 204, and an outlet portion 206. Cap body 202 includes a liquid sample passageway 208. Cap body 202 has an outer periphery configured to have a slidable gas and liquid seal with a side wall of sample vial 44. Inlet portion 204 is configured to receive a pressurized liquid sample from sample vial 44 where the liquid sample flows into liquid sample passageway 208. Vial cap 54 is configured to cap the open ended portion of the sample vial 44. Further, the vial cap 54 is also configured to be slidingly engaged with and to seal the side wall of the sample vial 44. The vial cap 54 has a generally concave portion that cooperatively mates with a generally convex lowermost portion of the sample vial 44.

Inlet portion can include a counterbore section 210 for holding a filter plug described herein. Counterbore section 210 is a cylindrical hole adjacent to outlet portion 206. The diameter of counterbore section 210 is greater than outlet portion 206. In an embodiment, the diameter of counterbore section 210 is sized to form a friction fit to hold a cylindrically shaped filter plug, as illustrated in FIG. 4. Alternatively, the filter plug can be mounted to the counterbore section with other types of fasteners.

Outlet portion 206 is configured to output the liquid sample from liquid sample passageway 208 that has passed through filter plug 42. Outlet portion 206 includes a plunger section 70 configured to receive a downward force into sample vial 44 to pressurize the liquid sample within sample vial 44. Plunger section 70 includes a socket configured to receive a plunger 33. Plunger 33 can have a geometric shape proximate to a tip 68 that mates with the socket of plunger section 70 to form a fluid tight seal, as illustrated in FIGS. 2 to 4. Plunger 33 is configured to apply a downward force to vial cap 54 and transfer the liquid sample through a hollow portion of plunger 33

The vial cap 54 does not begin to move until tip 68 of the plunger is fully seated in a plunger portion 70 (best shown in FIG. 3). When the plunger 33 begins to deploy, any air trapped in the sample vial 44 above the sample is discharged first. Once the delivery of the liquid sample 46 begins, it continues until the required sample amount has been drawn or the sample vial 44 is empty. In various embodiments, the sample vial and vial cap are configured to reduce "dead space" in the sample vial. The bottom of the exemplary vial has a shape corresponding to the cap such that substantially all of the fluid is displaced from the vial when the cap contacts the bottom.

Sample vial 44 and vial cap 54 are configured such that when the plunger 33 is fully deployed causing the vial cap 54 to remain in the lowest displacement position in the sample vial 44. Thus, the needle presses the vial cap 54 into the sample vial 44 but is withdrawn from the sample vial 44 without the vial cap 54. The vial cap remains in the sample vial with the sample pressurized below the cap. In one embodiment, the vial includes a bottom portion configured to fit tightly with vial cap 54. When plunger is retracted, the vial cap can be held in the bottom portion of the vial due to the tight fit and the plunger separates from the vial cap. After displacing the liquid sample through the filter plug, the vial cap along with the filter plug can be disposed as waste and not re-used.

Plunger 33 can also be referred to as a sample delivery needle or plunger needle and has a hollow cylindrical rod shaped structure. At one end of plunger 33, there is a needle tip 68. The other opposing end of plunger 33 can be used to transfer the liquid sample 46 to an analytical instrument.

Now that the vial cap have has described, the following will describe a method of using a vial cap to filter out and remove matrix components from a sample. An analyst will often have a large number of sample vials containing samples that need to be analyzed. However, before beginning the analysis testing, a sample pre-treatment may need to be performed to remove matrix components that can interfere with the analysis. Adding a matrix binding agent to the sample vial, mixing the sample vial, and filtering the matrix binding agent from the sample is a manual process that is time consuming and laborious. To implement an automated process, the matrix component binding filter plug can be used as a filter that is incorporated into the vial cap. The sample vial and vial cap are configured so that liquid flows through the vial cap and the filter at a relatively low pressure while at the same time efficiently binding a substantial portion of the matrix components. The pressure range for filtering sample may range from about 10 pounds per square inch to about 100 pounds per square inch.

FIG. 1 is a flow chart illustrating a method 100 of removing a matrix component from a liquid sample using a vial cap containing one of the matrix component binding filter plugs described herein. In a step 102, a liquid sample is added to a sample vial. Next, a vial cap is pushed through an inlet opening of the sample vial towards the bottom wall to pressurize the liquid sample within the sample vial, as shown in a step 104. The liquid sample is displaced into the inlet portion, through the filter plug, and out of the outlet portion, where the filter plug includes a polyethylene resin and a matrix component binding material (e.g., ion exchange material or a reversed-phase material), as shown in a step 106. At the same time of the displacing of step 106, a portion of the ions is removed from the liquid sample with the filter plug, as shown in a step 108. In an embodiment, about 50% or more of the matrix components can be removed from the liquid sample with a filter plug.

Once the sample has been pretreated to remove interfering matrix component, it can be subsequently analyzed with analytical instrumentation. After removing liquid sample 46 from the sample vial 44, the liquid sample 46 can be loaded onto a sample loop of an injection valve. Next, liquid sample from the sample loop can be injected into a chromatographic separation device. At least one analyte from the liquid sample can be separated from matrix components in the chromatographic separation device and the analyte can be detected at a detector.

Figure 5:
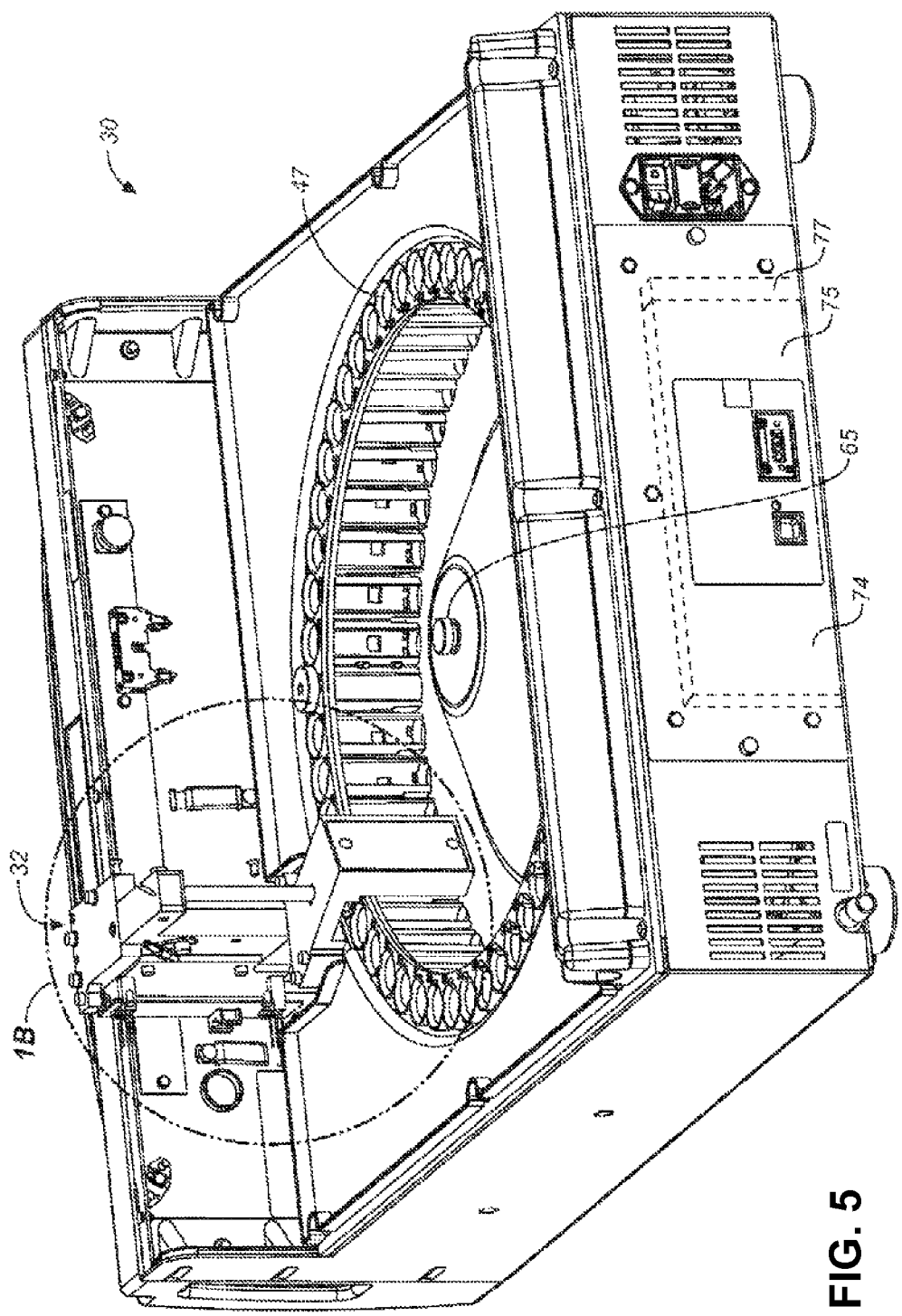
FIG. 5 is a partial perspective view of an autosampler suitable for dispensing liquid samples from a plurality of sample vials and that use the filter plugs described herein for removing matrix components.

FIG. 5 is a partial perspective view of an autosampler 30 suitable for dispensing liquid samples from a plurality of sample vials and for use with filter plugs described herein. Autosampler 30 is typically used when a large number of samples need to processed in an automated manner. A plurality of sample vials can be loaded on autosampler 30 in an array or carousel format. FIG. 5 illustrates a carousel of sample vial sockets 47 configured to hold a plurality of sample vials. A fluid delivery assembly 32 is configured to deploy and retract the plunger needle for one sample vial at a time as shown in a dotted circle 1B of FIG. 5. The carousel can increment a position by rotating around a hub with a drive motor 65 so that liquid can then be transferred from a subsequent sample vial. Autosampler 30 also includes a control system 74 that has a microprocessor 75 and a memory 77. Examples of commercially available autosamplers are the AS-DV, AS40, and ASM from Thermo Fisher Scientific.

Example 1

This Example illustrates the removal of divalent cations using a cation-exchange filter plug. A cylindrical filter plug of blended high density polyethylene (HDPE) and approximately 10 mg fully sulfonated, 16% crosslinked styrenesulfonate, sodium-form resin with a particle diameter of 35 μm was inserted into the counterbore portion of a vial cap. The cylindrical filter plug had an approximate diameter of 5 mm and a length of about 10 mm. The assembled vial cap with the cation exchange filter plug was sonicated in deionized water for 5 minutes.

A standard sample of six cations including 0.05 mg/L lithium, 0.2 mg/L sodium, 0.4 mg/L ammonium, 0.2 mg/L potassium, 0.2 mg/L magnesium and 1 mg/L calcium was loaded into a 5 mL sample vial. The assembled vial cap was inserted into the filled sample vial. Five milliliters of a sample (see Table 1) was pushed up through the filter plug in the vial cap and directed to a sample loop of an ion chromatograph for analysis using cation exchange chromatography. An eluent of 20 mM methanesulfonic acid was flowed at 0.5 mL/min through a cation exchange analytical column (part no. CS12A, 150×3-mm I.D., commercially available from Thermo Fisher Scientific) and an electrolytic suppressor (part no. CSRS 300, 2-mm I.D., commercially available from Thermo Fisher Scientific) followed by an electrical conductivity detector cell. The resulting chromatography peaks were integrated using CHROMELEON™ chromatography data system software (version 6.8, commercially available from Thermo Fisher Scientific).

Table 1 shows the results from a series of samples pretreated with the filter plug of Example 1 and analyzed using cation exchange chromatography.

| Sample | Description | Area, Sodium μS* min | % Removed | Area, Calcium μS* min | % Removed |
| --- | --- | --- | --- | --- | --- |
| 1 | 6 Cation Standard with no solid phase extraction | 0.039 | — | 0.18 | — |
| 2 | Water Flowed Through Filter Plug of Ex. 1 | 0.108 | — | 0.004 | — |
| 3 | 6 Cation Standard Flowed Through Filter Plug of Ex. 1 | 1.34 | * | 0.007 | 61 |

*Sodium increase due to displacement from the cation exchange resin by calcium

In Sample 1 of this Example, the six cation standard was analyzed in the ion chromatograph without a prior solid phase extraction where the resulting peak areas were proportional of the concentration of sodium and calcium in the six cation standard.

In Sample 2 of this Example, five milliliters of deionized water was flowed through the filter plug of this Example. This is a wash of the filter plug before use to remove calcium. Next, the filtered liquids were subsequently analyzed with the ion chromatograph. The amount of measured sodium was relatively high because the ion exchange material in the filter plug was in the sodium form. The amount of calcium was relatively low with respect to Sample 1 of this Example, but indicated that some residual calcium was on the filter plug.

In Sample 3 of this Example, five milliliters of the six cation standard was flowed through the filter plug of this Example. Next, the filtered liquids were subsequently analyzed with the ion chromatograph. The amount of measured sodium was relatively high because the ion exchange material in the filter plug was in the sodium form and the sodium was displaced by the more highly retained cations, most notably, calcium. The amount of calcium was decreased by 61% with respect to Sample 1 of this Example, which indicated that a substantial amount was retained by the filter plug.

Example 2

This Example illustrates the use of an ion-pairing reagent-functionalized reversed phase filter cap to remove cations from a sample. A cylindrical plug comprising blended high density polyethylene (HDPE) and 10 mg of 55% divinylbenzene resin with a particle diameter of 35 μm was inserted into the counterbore portion of a vial cap. The cylindrical filter plug had an approximate diameter of 5 mm and a length of about 10 mm. The assembled vial cap with the cation exchange filter plug was placed on a vacuum station and 2 mL of methanol was pushed up through the filter plug. Next, the assembled vial cap was sequentially flushed with a series of liquids, which 2 mL deionized water, 2 mL of 100 mM hexanesulfonic acid (HSA), and another aliquot of deionized water.

A standard sample of four cations including 5 ppb lithium, 20 ppb sodium, 20 ppb magnesium and 100 ppb calcium was loaded into a sample vial. The assembled vial cap was inserted into the filled sample vial. Two milliliters of a sample (see Table 2) was pushed up through the filter plug in the vial cap and directed to the ion chromatograph for cation exchange analysis. The cation exchange chromatography system conditions were similar to Example 1.

Table 2 shows the results from a series of samples pretreated with the filter plug of Example 2 and analyzed using cation exchange chromatography.

subsequently analyzed with the ion chromatograph. The amount of magnesium and calcium was decreased by 62% and 71%, respectively. This decrease was calculated relative to the cation levels in Sample 1 of this Example, which indicated that a substantial amount of divalent cations was retained by the filter plug with HSA treatment. The monovalent cation sodium was not retained by the filter plug of this Example, which was indicated by the approximate same level of sodium measured in Sample 1 and Sample 4.

Example 3

This Example illustrates the use of an anion exchange filter plug prepared with latex particles to remove anions from a sample. A cylindrical filter plug of blended high density polyethylene (HDPE) and approximately 10 mg fully sulfonated, 16% crosslinked styrenesulfonate, sodium-form resin with a particle diameter of 35 μm was inserted into the counterbore portion of a vial cap as described in Example 1. The cylindrical filter plug had an approximate diameter of 5 mm and a length of about 10 mm.

Five milliliters of deionized water was flowed through the filter plug using a vacuum. Five milliliters of a anion exchange latex, prepared in a manner similar to the description in example 3 of U.S. Pat. No. 5,324,752, was flowed through the filter plug using vacuum, followed by 5 milliliters of deionized water, 5 milliliters of a mixture of 50% methanol/50% deionized water, and 5 milliliters of deionized water.

| Sample | Description | Area, Sodium μS* min | % Removed | Area, Magnesium μS* min | % Removed | Area, Calcium μS* min | % Removed |
|---|---|---|---|---|---|---|---|
| 1 | 4 Cation Standard with no solid phase extraction | 0.01 | — | 0.028 | — | 0.007 | — |
| 2 | Deionized water blank | na | — | — | — | — | — |
| 3 | 4 Cation Standard Flowed Through Filter Plug of Ex. 2 without HSA | 0.01 | 0 | 0.029 | 0 | 0.007 | 0 |
| 4 | 4 Cation Standard Flowed Through Filter Plug of Ex. 2 with HSA | 0.01 | 0 | 0.011 | 62 | 0.002 | 71 |

In Sample 1 of this Example, the four cation standard was analyzed in the ion chromatograph without a prior solid phase extraction where the resulting peak areas were proportional of the concentration of sodium, magnesium, and calcium in the 4 cation standard.

In Sample 2 of this Example, two milliliters of deionized water was analyzed in the ion chromatograph without a prior solid phase extraction. The amounts of sodium, magnesium, and calcium measured through the chromatographic analysis were negligible.

In Sample 3 of this Example, two milliliters of the four cation standard was flowed through a filter plug without HSA treatment of this Example. Next, the filtered liquids were subsequently analyzed with the ion chromatograph. The measured sodium, magnesium, and calcium levels were essentially the same as Sample 1 indicating that cations were not retained by the filter plug without HSA treatment.

In Sample 4 of this Example, two milliliters of the four cation standard was flowed through the filter plug with HSA treatment of this Example. Next, the filtered liquids were A standard sample of six anions including 0.02 mg/L fluoride, 0.03 mg/L chloride, 0.1 mg/L nitrate, 0.15 mg/L sulfate, 0.15 mg/L phosphate, and 0.01% acetic acid was loaded into a 5 mL sample vial. The assembled vial cap was inserted into the filled sample vial. Five milliliters of sample (see Table 3) was pushed through the filter plug in the vial cap and directed to the ion chromatograph for an ion exchange analysis. An eluent of 40 mM potassium hydroxide flowed at 0.3 mL/minute through an anion exchange analytical column (part no. AS15, 150×3 mm I.D.) and an electrolytic suppressor (part no. ASRS 2-mm) both supplied by Thermo Fisher Scientific. An electrical conductivity detector cell was used to measure the anions.

Table 3 shows the results from a series of samples pretreated with the filter plug of Example 3 and analyzed using anion exchange chromatography.

| Sample | Description | Area, Sulfate µS* min | % Removed | Area, Phosphate µS* min | % Removed |
|---|---|---|---|---|---|
| 1 | 6 Anion Standard With No Solid Phase Extraction | 0.15 | — | 0.03 | — |
| 2 | Water Flowed Through Filter Plug of Ex. 3 | 0.005 | — | 0 | — |
| 3 | 6 Anion Standard pH 5 Flowed Through Filter Plug of Ex. 3 | 0.06 | 60 | 0 | 100 |

In Sample 1 of this Example, the six anion standard was analyzed in the ion chromatograph without a prior solid phase extraction where the resulting peak areas were proportional of the concentration of sulfate and phosphate in the six anion standard.

In Sample 2 of this Example, five milliliters of deionized water was flowed through the filter plug of this Example. Next, the filtered liquids were subsequently analyzed with the ion chromatograph. A relatively low amount of sulfate was measured indicating that some residual sulfate was likely on the filter plug. No phosphate was measured from the filtered water sample.

In Sample 3 of this Example, five milliliters of the six anion standard was flowed through the filter plug of this Example. Next, the filtered liquids were subsequently analyzed with the ion chromatograph. The amount of sulfate was decreased by 60% with respect to Sample 1 of this Example, which indicated that a substantial amount was retained by the filter plug. Similarly, the amount of phosphate was decreased by 100% with respect to Sample 1 of this Example, which indicated that a substantial amount was retained by the filter plug.

Example 4

This Example illustrates the use of a reversed-phase filter plug prepared with divinylbenzene resin to remove hydrophobic material such as sodium lauryl sulfate (SLS) from an aqueous sample. A cylindrical plug from Example 2 was used in a vial cap for this example.

The assembled vial cap was inserted into the filled sample vial. Five milliliters of a 100 mg/L sodium lauryl sulfate sample was pushed up through the filter plug in the vial cap and directed to the liquid chromatograph for surfactant analysis. An eluent of 75% acetonitrile and 25% of 100 mM ammonium acetate at pH 5.4 was flowed at 0.25 mL/min through a reversed phase analytical column (part no. Acclaim Surfactant, 150×2-mm I.D., commercially available from Thermo Fisher Scientific) followed by detection using a mass spectrometer (part no. MSQ Plus, commercially available from Thermo Fisher Scientific). The resulting chromatography peaks were integrated using CHROMELEON™ chromatography data system software (version 6.8, commercially available from Thermo Fisher Scientific). The amount of SLS injected into the analytical system was the amount of SLS that was not captured by the filter plug in the vial cap. This amount corresponded to a removal of 98% of the SLS from the sample. The removal of the matrix components in this Example demonstrates that analysis of common anions such as chloride and sulfate can be performed.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A vial cap for removing a matrix component from a liquid sample and transferring the liquid sample in a sample vial to an injection valve at the same time, the vial cap comprising:
    a cap body including a liquid sample passageway, and an outer periphery configured to have a slidable gas and liquid seal with a side wall of a sample vial, the sample vial including a side wall, a bottom wall, and an inlet opening;
    an inlet portion configured to receive a pressurized liquid sample from the sample vial where the liquid sample flows into the liquid sample passageway, the inlet portion including a counterbore section, the counterbore section holding a filter plug, the filter plug comprising high density polyethylene resin particles fused together with a reversed-phase material, the reversed-phase material physically entrapped within a void volume in the fused high density polyethylene;
    an outlet portion configured to output the liquid sample from the liquid sample passageway that has passed through the filter plug, the outlet portion including a plunger section configured to receive a downward force into a sample vial to pressurize the liquid sample within the sample vial, in which the reversed-phase material comprises a divinylbenzene resin treated with an ion pairing agent selected from the group consisting of a hexane sulfonate, octane sulfonate, dodecane sulfonate, tetrapropylammonium, tetrabutylammonium, tetrapentylammonium, trifluoroacetate, heptafluorobutyrate, dodecylsulfate, and combinations thereof.

2. The vial cap of claim 1, in which the ion pairing agent comprises hexane sulfonate.

3. The vial cap of claim 1, in which the ion pairing agent comprises octane sulfonate.

4. The vial cap of claim 1, in which the ion pairing agent comprises dodecane sulfonate.

5. The vial cap of claim 1, in which the ion pairing agent comprises dodecylsulfate.

6. The vial cap of claim 1, in which the reversed-phase material includes a plurality of particles.

* * * * *